United States Patent [19]

Terasaka et al.

[11] Patent Number: 6,005,134
[45] Date of Patent: Dec. 21, 1999

[54] PROCESS FOR THE PREPARATION OF ALIPHATIC NITRILES

[75] Inventors: Michio Terasaka; Yasuyuki Mimura; Hiroshi Abe, all of Wakayama, Japan

[73] Assignee: Kao Corporation, Tokyo, Japan

[21] Appl. No.: 09/314,118

[22] Filed: May 19, 1999

[30] Foreign Application Priority Data

Jun. 25, 1998 [JP] Japan .................................. 10-178415
Jun. 25, 1998 [JP] Japan .................................. 10-178416

[51] Int. Cl.$^6$ ................................................. C07C 253/00
[52] U.S. Cl. ............................................ 558/311; 558/313
[58] Field of Search ..................................... 558/311, 313

[56] References Cited

U.S. PATENT DOCUMENTS 2,177,619 10/1939 Nicodemus et al. ..................... 558/311
2,493,637 1/1950 Niederhauser .

FOREIGN PATENT DOCUMENTS 704 494 4/1941 Germany .
58-39653 8/1983 Japan .
4-208260 7/1992 Japan .

*Primary Examiner*—Johann Richter
*Assistant Examiner*—Joseph Murray
*Attorney, Agent, or Firm*—Oblon, Spivak, McClelland, Maier & Neustadt, P.C.

[57] ABSTRACT

The present invention provides a process for preparing a high-quality aliphatic nitrile in a high yield at a low cost without the dissolution of a catalyst in the product, which comprises reacting an aliphatic carboxylic acid, a lower alkyl ester thereof or a fatty acid glyceride with ammonia in the presence of a solid catalyst which exhibits a high activity even at a reaction temperature of as low as 300° C. or below and is difficultly soluble in the reaction fluid; and a process for the preparation of amines by hydrogenating the aliphatic nitrile prepared by the above process. Namely, the present invention provides a process for the preparation of an aliphatic nitrile by reacting an aliphatic carboxylic acid, a lower alkyl ester thereof or a fatty acid glyceride with ammonia in the presence of a composite oxide catalyst comprising titanium oxide as the main component; and a process for the preparation of amines by hydrogenating the aliphatic nitrile prepared by the above process.

5 Claims, No Drawings

PROCESS FOR THE PREPARATION OF ALIPHATIC NITRILES

BACKGROUND ART

1. Technical Field

The present invention relates to a process for preparing high-quality aliphatic nitriles in high yields.

2. Description of the Prior Art

In general, aliphatic nitriles are industrially produced by the reaction of aliphatic carboxylic acids or derivatives thereof with ammonia. The reaction are broadly classified into gas-phase and liquid-phase processes. According to the gas-phase process, the reaction is conducted by preliminarily vaporizing an aliphatic carboxylic acid or a derivative thereof and bringing the vapor into contact with ammonia at a temperature of 250 to 600° C. in the presence of a catalyst having a dehydrating activity, e.g., oxide of Zr, Ta, Ga, In, Sc, Nb, Hf, Fe, Zn or Sn (JP-A 4-208260), aluminum oxide, silica gel, thorium oxide or titanium oxide. However, the gas-phase process involves the vaporization of the starting material and are therefore disadvantageous in that the energy cost is higher than that of the liquid-phase process.

On the other hand, the reaction is also frequently conducted according to the liquid-phase process in a batch-wise or continuous manner by heat-melting an aliphatic carboxylic acid or a derivative thereof in the presence of a catalyst and bubbling gaseous ammonia thereinto. Known catalysts for the reaction include aliphatic carboxylic acid salts of cobalt (U.S. Pat. No. 2,493,637), iron and iron compounds (JP-A 58-39653), zinc oxide, kaolin (DE-C 704494), and so on. Although these catalysts exhibit high catalytic activities at a reaction temperature of 300° C. or below, they are soluble in the reaction fluid, so that the use of such a catalyst involves the separation and recovery thereof from the reaction product by specific operations, which unfavorably brings about a lowering in the yield of distillation or an increase of waste.

An object of the present invention is to provide a process for preparing a high-quality aliphatic nitrile in a high yield at a low cost without the dissolution of a catalyst in the product, which comprises reacting an aliphatic carboxylic acid, a lower alkyl ester thereof or a fatty acid glyceride with ammonia in the presence of a solid catalyst which exhibits a high activity at a reaction temperature of 300° C. or below and is difficultly soluble in the reaction fluid.

SUMMARY OF THE INVENTION

The inventors of the present invention have found that a composite oxide catalyst comprising titanium oxide as the main component exhibits a high catalytic activity even at a reaction temperature of as low as 300° C. or below and is difficultly soluble in the reaction fluid. The present invention has been accomplished on the basis of this finding.

Namely, the present invention relates to a process for the preparation of an aliphatic nitrile by reacting an aliphatic carboxylic acid, a lower alkyl ester thereof or a fatty acid glyceride with ammonia in the presence of a composite oxide catalyst comprising titanium oxide as the main component.

Further, the present invention relates also to a process for the preparation of an amine compound by hydrogenating the nitrile prepared by the above process.

The term "composite oxide" used in this description refers to an oxide comprising two or more metals which are coexistent with each other either in the catalyst body or on the surface thereof.

More precisely, the present invention provides a process for the preparation of an aliphatic nitrile, which comprises the step of reacting at least one compound selected from among (1) $C_6$–$C_{22}$ aliphatic monocarboxylic acids, (2) $C_6$–$C_{22}$ aliphatic dicarboxylic acids, (3) $C_1$–$C_5$ alkyl esters of $C_6$–$C_{22}$ aliphatic monocarboxylic acids, (4) $C_1$–$C_5$ alkyl esters of $C_6$–$C_{22}$ aliphatic dicarboxylic acids, and (5) aliphatic glycerides with ammonia in the presence of a composite oxide catalyst comprising titanium and at least one other metal.

As compared with the process of the prior art, the process of the present invention is freed from the problematic dissolution of a catalyst in the product by virtue of the use of a composite oxide catalyst which exhibits a high activity and is difficultly soluble in the reaction fluid to give high-quality aliphatic nitriles in high yields, thus being industrially useful.

DETAILED DESCRIPTION OF THE PREFERRED EMBODIMENTS

The aliphatic carboxylic acid to be used in the present invention is selected from among linear and branched $C_6$–$C_{22}$ saturated and unsaturated aliphatic mono- and di-carboxylic acids, which may be used each alone or as a mixture of two or more of them.

Specific examples of the aliphatic carboxylic acid include caproic acid, caprylic aicd, capric acid, lauric acid, myristic acid, palmitic acid, stearic acid, arachic acid, behenic acid, dimethyloctanoic acid, butylheptylnonanoic acid, hexenoic acid, octenoic acid, decenoic acid, dodecenoic acid, tetradecenoic acid, hexadecenoic acid, octadecenoic acid, eicosenoic acid, docosenoic acid, adipic acid, azelaic acid, sebacic acid, decamethylenedicarboxylic acid, hexadecamethylenedi-carboxylic acid and octadecamethylenedicarboxylic acid.

The aliphatic carboxylic acid lower alkyl ester to be used in the present invention is selected from among lower alkyl esters of linear and branched $C_6$–$C_{22}$ saturated and unsaturated aliphatic monocarboxylic acids and di(lower alkyl) esters of linear and branched $C_6$–$C_{22}$ saturated and unsaturated aliphatic dicarboxylic acids. The term "lower alkyl" used in this description refers to $C_1$–$C_5$ alkyl, and specific examples thereof include methyl, ethyl, propyl and isopropyl, among which methyl is particularly preferable. These aliphatic carboxylic acid lower alkyl esters may be used each alone or as a mixture of two or more of them.

Specific examples of the aliphatic carboxylic acid lower alkyl esters include methyl caproate, methyl caprylate, methyl caprate, methyl laurate, methyl myristate, methyl palmitate, methyl stearate, methyl arachate, methyl behenate, methyl dimethyloctanoate, methyl butylheptylnonanoate, methyl hexenoate, methyl octenoate, methyl decenoate, methyl dodecenoate, methyl tetradecenoate, methyl hexadecenoate, methyl octadecenoate, methyl eicosenoate, methyl docosenoate, dimethyl adipate, dimethyl azelate, dimethyl sebacate, dimethyl deca-methylenedicarboxylate, dimethyl hexadecamethylene-dicarboxylate and dimethyl octadecamethylenedi-carboxylate.

The aliphatic glycerides to be used in the present invention may preferably include a glycerin ester of a linear or branched, $C_6$–$C_{22}$, saturated or unsaturated, aliphatic monocarboxylic acid. Among the glycerin esters, in particular, natural oils and fats of animals or plants are effective. The aliphatic glyceride may be used alone or in a mixture of different glycerin esters.

Examples of these aliphatic glycerides may be beef tallow, pork tallow, soybean oil, cotton seed oil, rapeseed oil, coconut oil, palm oil, palm kernel oil and tall oil.

The catalyst to be used in the present invention is a composite oxide catalyst comprising titanium oxide as the main component, preferably one composed essentially of titanium oxide and at least one member selected from the group consisting of oxides of silicon, niobium, zirconium, tantalum, gallium and germanium, particularly preferably one composed essentially of titanium oxide and one oxide selected from among silica, niobium oxide and zirconium oxide. It is preferable from catalytic activity that the content of oxides other than titanium oxide in the composite oxide catalyst is 1 to 25% by weight, still preferably 1 to 15% by weight.

Further, the titanium oxide content of the composite oxide catalyst according to the present invention in terms of titanium at metallic state is preferably 44 to 75% by weight, still preferably 50 to 75% by weight, while that in terms of the titanium oxide is preferably 75 to 99% by weight, still preferably 85 to 99% by weight.

The process for preparing the catalyst to be used in the present invention is not particularly limited, but may be any process by which titanium oxide together with other metal oxide can form a complex. Such a process includes deposition, coprecipitation, alkoxide methods and impregnation. It is preferable to calcinate the catalyst at a temperature of 500° C. or below.

The process of the present invention can be conducted either by the use of a suspended-bed reactor in a batch-wise, semi-batch-wise or continuous manner or by the use of a fixed-bed flow reactor. The reaction temperature is selected preferably within the range of 180 to 350° C., still preferably within the range of 250 to 300° C. The reaction is generally conducted in a slightly pressurized state, though it may be conducted under normal pressure. When the reaction is conducted by the use of a suspended-bed reactor in a batch-wise, semi-batch-wise or continuous manner, the amount of the composite oxide catalyst to be used is preferably 0.1 to 10% by weight, still preferably 0.3 to 3% by weight based on the aliphatic carboxylic acid, lower alkyl ester thereof or fatty acid glyceride used, while when the reaction is conducted by the use of a fixed-bed flow reactor, the average residence time of the reactant mixture in the catalyst bed is preferably one second to 10 minutes.

Meanwhile, the preparation of an amine from the nitrile prepared by the above process through hydrogenation is conducted under the following conditions:

hydrogenation catalyst: Raney Ni or Raney Co reaction temp.: 80 to 250° C.

hydrogen pressure: 0.1 to 5 MPa reaction assistant: alkali metal hydroxide or ammonia.

EXAMPLES A1 TO A4

COMPARATIVE EXAMPLES A1 TO A3

EXAMPLES B1 TO B4 AND COMPARATIVE EXAMPLES B1 TO B3

Titanium tetraisopropoxide, tetraethyl ortho-silicate and isopropanol which was as solvent were charged into a flask so as to give a titanium oxide/silica weight ratio specified in Tables 1A and 1B. The temperature of the contents was raised to 80° C., and then six times as much ion-exchanged water as the metal alkoxide component by mole was dropped into the flask under stirring. After the completion of the dropping, the contents were stirred at that temperature for 5 hours and filtered to recover a catalyst precursor. This precursor was washed with ion-exchanged water, filtered, dried at 110° C. and calcinated at 300° C. for 3 hours. Thus, composite oxide catalysts according to the present invention were prepared.

Examples A1 to A4 will now be described. In a four-necked flask equipped with a stirrer, a gas inlet tube, a thermometer and a dehydration device, 5.0 g of each of the composite oxide catalysts prepared above was mixed with 500 g of stearic acid, and then gaseous ammonia was introduced into the flask at 260° C. and at a rate of 1050 ml/min over a period of 5 hours to conduct a reaction. The reaction product thus obtained was analyzed for composition by gas chromatography [gas chromatograph: HEWLETT PACKARD Series 5890; and column: DB-5, aproduct of J&W (bore diameter×length: 0.53 mm×15 m)] to determine the amount of nitrile formed. For comparison, the preparation of a nitrile was conducted under the same conditions as those employed above except that the catalyst was replaced by a catalyst prepared by repeating the same procedure as described above which essentially consisted of titanium oxide or silica alone or a catalyst prepared by mixing both physically which had a weight ratio of titanium oxide to silica of 95:5. These are shown as Comparative Examples A1 to A3. The results are given in Table 1A. When any of the catalysts according to the present invention was used, the reaction proceeded speedily and the elemental analysis of the products by ICP emission spectrometry revealed that the contents of titanium and silicon therein were below the detection limits respectively.

In the above gas chromatographic analysis, squalane was used as the internal standard. The use of squalane as the internal standard was made also in the gas chromatographic analyses which will be described below.

Then, Examples B1 to B4 will now be described. The same procedures as those of Examples A1 to A4 were repeated except that the stearic acid was replaced by methyl stearate and that gaseous ammonia was introduced at a rate of 1100 ml/min instead of 1050 ml/min over a period of 6 hours instead of 5 hours. For comparison, the preparation of a nitrile was conducted under the same conditions as those employed above except that the catalyst was replaced by a catalyst prepared by repeating the same procedure as described above which essentially consisted of titanium oxide or silica alone or a catalyst prepared by mixing both physically which had a weight ratio of titanium oxide to silica of 95:5. These are shown as Comparative Examples B1 to B3. The results are given in Table 1B. When any of the catalysts according to the present invention was used, the reaction proceeded speedily and the elemental analysis of the product by ICP emission spectrometry revealed that the contents of titanium and silicon therein were below the detection limits respectively.

EXAMPLES A5 AND A6

Composite oxide catalysts were prepared by repeating the same procedure as that of Example A1, except that zirconium tetrapropoxide was used instead of the tetraethyl orthosilicate and that the weight ratio of titanium oxide to zirconium oxide was adjusted to a value specified in Table 1A. The preparation of a nitrile was conducted under the same conditions as those employed in Example A1 except that the catalyst was replaced by each of the catalysts prepared above. The products thus obtained were analyzed in a similar manner to that of Example A1, and the results are given in Table 1A. The contents of titanium and zirconium in each product were below the detection limits respectively.

EXAMPLES A7 TO A9

Composite oxide catalysts were prepared by repeating the same procedure as that of Example A2 except that niobium pentaethoxide, tantalum pentaethoxide or gallium tripropoxide was used instead of the tetraethyl orthosilicate. The preparation of a nitrile was conducted under the same conditions as those employed in Example A1 except that the catalyst was replaced by each of the catalysts prepared above. The products thus obtained were analyzed in a similar manner to that of Example A1, and the results are given in Table 1A. The contents of metals resulting from the catalyst in each product were below the detection limits respectively.

EXAMPLES B5 TO B9

Composite oxide catalysts were prepared by repeating the same procedure as that of Example B2 except that zirconium tetrapropoxide, niobium pentaethoxide, tantalum pentaethoxide, gallium triisopropoxide or germanium tetraethoxide was used instead of the tetraethyl orthosilicate. The preparation of a nitrile was conducted under the same conditions as those employed in Example B1 except that the catalyst was replaced by each of the catalysts prepared above. The products thus obtained were analyzed in a similar manner to that of Example B1, and the results are given in Table 1B. The contents of metals resulting from the catalyst in each product were below the detection limits respectively.

EXAMPLE A10

The preparation of a nitrile was conducted under the same conditions as those employed in Example A1, except that the composite oxide catalyst prepared in Example A2 which had a titanium oxide/silica weight ratio of 95:5 was used and that gaseous ammonia was introduced at a reaction temperature of 300° C. over a period of 3 hours. The product was analyzed in a similar manner to that of Example A1, and the result is given in Table 1A. The contents of titanium and silicon in the product were below the detection limits respectively.

EXAMPLE B10

The preparation of a nitrile was conducted under the same conditions as those employed in Example B1, except that the composite oxide catalyst prepared in Example B2 which had a titanium oxide/silica weight ratio of 95:5 was used and that the same reaction temperature and introduction time of gaseous ammonia as those of Example A1 were employed. The product was analyzed in a similar manner to that of Example B1, and the result is given in Table 1B. The contents of titanium and silicon in the product were below the detection limits respectively.

TABLE 1A

| | Compn. of catalyst (wt. ratio) | Reaction temp. (° C.) | Reaction time (hr) | Yield of nitrile (wt. %) |
|---|---|---|---|---|
| Examples | | | | |
| A1 | titanium oxide/silica (99:1) | 260 | 5 | 83.2 |
| A2 | Titanium oxide/silica (95:5) | 260 | 5 | 91.1 |
| A3 | Titanium oxide/silica (85:15) | 260 | 5 | 83.7 |
| A4 | Titanium oxide/silica (75:25) | 260 | 5 | 82.0 |
| Comparative Examples | | | | |
| A1 | Titanium oxide/silica (100:0) | 260 | 5 | 77.8 |
| A2 | Titanium oxide/silica (0:100) | 260 | 5 | 47.8 |
| A3 | Titanium oxide/silica* (95:5) | 260 | 5 | 77.3 |
| Examples | | | | |
| A5 | Titanium oxide/zirconium oxide (95:5) | 260 | 5 | 88.2 |
| A6 | Titanium oxide/zirconium oxide (85:15) | 260 | 5 | 83.0 |
| A7 | titanium oxide/niobium oxide (95:5) | 260 | 5 | 85.0 |
| A8 | titanium oxide/tantalum oxide (95:5) | 260 | 5 | 88.1 |
| A9 | titanium oxide/potassium oxide (95:5) | 260 | 5 | 88.8 |
| A10 | Titanium oxide/silica (95:5) | 300 | 3 | 98.8 |

*: catalyst prepared by physically mixing powdered titanium oxide with powdered silica

TABLE 1B

| | Compn. of catalyst (wt. ratio) | Reaction temp. (° C.) | Reaction time (hr) | Yield of nitrile (wt. %) |
|---|---|---|---|---|
| Examples | | | | |
| B1 | Titanium oxide/silica (99:1) | 260 | 6 | 81.7 |
| B2 | Titanium oxide/silica (95:5) | 260 | 6 | 86.5 |
| B3 | Titanium oxide/silica (85:15) | 260 | 6 | 80.3 |
| Comparative Examples | | | | |
| B1 | Titanium oxide/silica (100:0) | 260 | 6 | 77.1 |

TABLE 1B-continued

|  | Compn. of catalyst (wt. ratio) | Reaction temp. (° C.) | Reaction time (hr) | Yield of nitrile (wt. %) |
|---|---|---|---|---|
| B2 | Titanium oxide/silica (0:100) | 260 | 6 | 42.9 |
| B3 | Titanium oxide/silica* (95:5) | 260 | 6 | 76.8 |
| Examples | | | | |
| B5 | Titanium oxide/ zirconium oxide (95:5) | 260 | 6 | 82.9 |
| B6 | titanium oxide/niobium oxide (95:5) | 260 | 6 | 82.9 |
| B7 | titanium oxide/tantalum oxide (95:5) | 260 | 6 | 84.6 |
| B8 | titanium oxide/ potassium oxide (95:5) | 260 | 6 | 85.8 |
| B9 | titanium oxide/ germanium oxide (95:5) | 260 | 6 | 81.2 |
| B10 | Titanium oxide/silica (95:5) | 300 | 3 | 96.0 |

*: catalyst prepared by physically mixing powdered titanium oxide with powdered silica

EXAMPLE A11

The preparation of a nitrile was conducted under the same conditions as those employed in Example A1, except that the composite oxide catalyst prepared in Example A2 which had a titanium oxide/silica weight ratio of 95:5 was used and that lauric acid was used instead of the stearic acid. The product was analyzed in a similar manner to that of Example A1, and the yield of laurylonitrile was 91.8% by weight. The contents of titanium and silicon in the product were below the detection limits respectively.

EXAMPLE B11

The preparation of a nitrile was conducted under the same conditions as those employed in Example B1, except that the composite oxide catalyst prepared in Example B2 which had a titanium oxide/silica weight ratio of 95:5 was used and that methyl laurate was used instead of the methyl stearate. The product was analyzed in a similar manner to that of Example B1, and the yield of laurylonitrile was 86.3% by weight. The contents of titanium and silicon in the product were below the detection limits respectively.

EXAMPLE A12

An unfired powder was prepared by repeating the same procedure as that of Example A2 with the titanium oxide/silica weight ratio adjusted to 95:5. This powder was molded by extrusion and fired at 300° C. for 3 hours, and 1.0 g of the molded catalyst thus prepared was packed into the central section of a stainless steel tubular reactor having a bore diameter of 10 mm and a length of 500 mm. Gaseous ammonia and stearic acid were fed into the reactor from the top thereof at rates of 706 ml/hr and 1.2 g/hr respectively, and reacted at 250° C. under normal pressure. The obtained reaction mixture was subjected to gas-liquid separation and analyzed by gas chromatography in a similar manner to that of Example A1. The yield of stearonitrile was 99.1% by weight. The contents of titanium and silicon in the product were below the detection limits respectively.

EXAMPLE B12

An unfired powder was prepared by repeating the same procedure as that of Example B2 with the titanium oxide/silica weight ratio adjusted to 95:5. This powder was converted into a molded catalyst in a similar manner to that of Example A12, and 1.0 g of the molded catalyst was packed into the central section of the same reactor as that used in Example A12. Gaseous ammonia and methyl stearate were fed into the reactor from the top thereof at rates of 927 ml/hr and 1.2 g/hr respectively, and reacted at 250° C. under normal pressure. The obtained reaction mixture was subjected to gas-liquid separation and analyzed by gas chromatography in a similar manner to that of Example B1. The yield of stearonitrile was 98.9% by weight. The contents of titanium and silicon in the product were below the detection limits respectively.

COMPARATIVE EXAMPLE C1

The preparation of a nitrile was conducted under the same conditions as those of Example A1 except that zinc oxide (a product of Katayama Chemical Industries Co., Ltd., reagent of special grade) was used as the catalyst. The product was analyzed in a similar manner to that of Example A1. The result is given in Table 1C. The content of zinc in the product was 0.8%.

COMPARATIVE EXAMPLE C2

A catalyst essentially consisting of zirconium oxide was prepared by repeating the same procedure as that of Example A1 except that zirconium tetrapropoxide was used as the raw material. The preparation of a nitrile was conducted under the same conditions as those employed in Example A1 except that the catalyst prepared above was used. The reaction product thus obtained was analyzed in a similar manner to that of Example A1, and the result is given in Table 1C. The content of zirconium in the product was below the detection limit.

COMPARATIVE EXAMPLE C3

The preparation of a nitrile was conducted under the same conditions as those of Example B1 except that zinc oxide (a product of Katayama Chemical Industries Co., Ltd., reagent of special grade) was used as the catalyst. The product was analyzed in a similar manner to that of Example B1. The result is given in Table 1C. The content of zinc in the product was 0.8%.

COMPARATIVE EXAMPLE C4

A catalyst essentially consisting of zirconium oxide was prepared by repeating the same procedure as that of Example B1 except that zirconium tetrapropoxide was used as the raw material. The preparation of a nitrile was conducted under the same conditions as those employed in Example B1 except that the catalyst prepared above was used. The reaction product thus obtained was analyzed in a similar manner to that of Example B1, and the result is given in Table 1C. The content of zirconium in the product was below the detection limit.

TABLE 1C

| Comparative Example | Catalyst | Reaction temp. (° C.) | Reaction time (hr) | Yield of nitrile (wt. %) |
| --- | --- | --- | --- | --- |
| C1 | zinc oxide | 260 | 5 | 96.2 |
| C2 | zirconium oxide | 260 | 5 | 50.8 |
| C3 | zinc oxide | 260 | 6 | 84.9 |
| C4 | zirconium oxide | 260 | 6 | 50.2 |

EXAMPLE D1

In a four-necked flask equipped with a stirrer, a gas inlet tube, a thermometer and a dehydration device, 10.0 g of the composite oxide prepared in Example A2 which had a titanium oxide/silica weight ratio of 95:5 was mixed with 500 g of beef tallow, followed by the introduction of gaseous ammonia at a rate of 1050 ml/min over a period of 5 hours at 300° C. The reaction product thus obtained was converted into a derivative through the reaction with a silylating agent (TMSI-H, a product of GL Sciences Inc.), and analyzed for composition by gas chromatography [gas chromatograph: HEWLETT PACKARD Series 6890; and column: Ultra ALLOY+−1 (HT) (bore diameter: 0.25 mm, and length: 15 mm)]. The yield of beef tallow nitrile was 59.2% by weight. The contents of metals resulting from the catalyst in the product were below the detection limits respectively.

What is claimed is:

1. A process for the preparation of an aliphatic nitrile, which comprises the step of reacting at least one compound selected from the group consisting of
   (1) $C_6$–$C_{22}$ aliphatic monocarboxylic acids,
   (2) $C_6$–$C_{22}$ aliphatic dicarboxylic acids,
   (3) $C_1$–$C_5$ alkyl esters of $C_6$–$C_{22}$ aliphatic monocarboxylic acids,
   (4) $C_1$–$C_5$ alkyl esters of $C_6$–$C_{22}$ aliphatic dicarboxylic acids, and
   (5) aliphatic glycerides
with ammonia in the presence of a composite oxide catalyst comprising titanium and at least another metal.

2. A process for the preparation of an aliphatic nitrile according to claim 1, wherein the metal is selected from the group consisting of silicon, niobium, zirconium, tantalum, gallium and germanium.

3. A process for the preparation of an aliphatic nitrile according to claim 1, wherein the oxide of the metal other than titanium is contained in the composite oxide catalyst in an amount of 1 to 25% by weight.

4. A process for the preparation of an aliphatic nitrile according to claim 1, wherein the oxide of the metal other than titanium is contained in the composite oxide catalyst in an amount of 1 to 15% by weight.

5. A process for the preparation of an aliphatic nitrile according to claim 1, wherein the reaction is conducted by a liquid-phase process.

* * * * *